United States Patent [19]
Goudzenko et al.

[11] Patent Number: 5,817,621
[45] Date of Patent: Oct. 6, 1998

[54] EXTERNAL REMEDY POSSESSING TROPHOPROTECTIVE EFFECT

[76] Inventors: Janna Prokofievna Goudzenko; Elena Valerievna Korotkaia, both of 7 Raisa Okipna Str. Apt. 48, 253167 Kyiv, Ukraine

[21] Appl. No.: 776,575

[22] PCT Filed: Aug. 3, 1995

[86] PCT No.: PCT/UA95/00005

§ 371 Date: Feb. 3, 1997

§ 102(e) Date: Feb. 3, 1997

[87] PCT Pub. No.: WO96/05797

PCT Pub. Date: Feb. 29, 1996

[30] Foreign Application Priority Data

Aug. 3, 1994 [UA] Ukraine .................................. 94086487

[51] Int. Cl.$^6$ ........................ A61K 31/34; A61K 31/195; A61K 31/125; A61K 31/07
[52] U.S. Cl. ..................................................... 514/2
[58] Field of Search ................................ 514/2, 159, 167, 514/304, 474, 561, 567, 692, 725

[56] References Cited

U.S. PATENT DOCUMENTS

| | | | |
|---|---|---|---|
| 4,952,560 | 8/1990 | Kigasawa et al. | 514/2 |
| 5,446,070 | 8/1995 | Mantelle | 514/772.6 |

FOREIGN PATENT DOCUMENTS

| | | |
|---|---|---|
| 0 530 862 A2 | 3/1989 | European Pat. Off. . |
| 0 378 936 A2 | 7/1989 | European Pat. Off. . |
| 0 330 583 A2 | 8/1989 | European Pat. Off. . |
| 2 492 659 A1 | 4/1982 | France . |
| 2 557 452 A1 | 7/1985 | France . |
| 2 521 005 A1 | 8/1988 | France . |
| 1782590 A1 | 12/1990 | U.S.S.R. . |
| 1804835 A1 | 3/1993 | U.S.S.R. . |
| WO 93/10755 | 6/1993 | WIPO . |

OTHER PUBLICATIONS

Skripkin, et al. Handbook on Children's Dermatology, Moscow, "Medicina", pp. 64–66, 227, 314, (1983).
Koroleva, et al. "Reference Book on Medical Cosmetology", Zdorovje, pp. 86–97, (1989).
Ptcholkina et al. Reference Book on Medical Cosmetology, Leningrad, "Medicina", pp. 15–16, (1978).
Abakhadze, et al. (ed.) Reference Book on Medical Cosmetology, Moscow, "Medicina", p. 71, (1975).

*Primary Examiner*—Kimberly Jordan
*Attorney, Agent, or Firm*—Foley & Lardner

[57] ABSTRACT

A dermatological composition for external use comprising a lipid ointment base, vitamin A, a salicylic acid or a derivative thereof, D-camphor, a biogenic GABAergic substance, a biogenic dopaminergic substance, M-cholinolytics, pancreatin, ascorbic acid, pantothenic acid calcium salt, vitamin D2, and water is disclosed. The composition can optionally contain at least one of an antihistaminic agent, such as dimedrole, dimexide, and a fragrant substance, such as lavender oil or rose oil. The composition is useful as a nutritional skin cream for restoring the physiological functions of the skin.

6 Claims, No Drawings

EXTERNAL REMEDY POSSESSING TROPHOPROTECTIVE EFFECT

This invention relates to the medical field, and particularly to cosmetology, to provide new effective cosmetic preparations, such as nutritional skin creams, which restores physiological functions to the skin.

BACKGROUND OF THE INVENTION

Searching for preparations and methods to maintain skin nutrition is an important problem in cosmetology. The skin's metabolism is the basis for its functional activity and regenerative ability.

The human skin is in close relationship with the internal organs and is also in constant interaction with the environment. Human skin acts as the interface between the environment and body and is always directly influenced by different environmental factors and variable parameters of human internal system. The skin regulatory mechanisms are always active and ready to induce systemic changes necessary to normalize any pathological event concerning skin morphology and activities. The trophic processes, which are responsible for the adequate consumption of energetic and plastic substances according to the increased needs of the skin, ensure morphological and functional stability of skin structures. The skin's nutrition is a determinative factor in the skin's viability, leading to healthy skin with the characteristics of elasticity, turgor, humidity, pigmentation, etc.

The skin uses not only its own resources, but also the resources from the entire body. There are presently different nutritional creams with different trophotropic and metabolic properties.

A well known cosmetic remedy containing equal quantities of lanolin, plant oil and water causes decreased heat emission from the skin, increased skin temperature; increased blood flow causes skin hyperemia activating skin metabolism followed by optimization of the skin functions (Yu. K. Skripkin, F. A. Zvierkova, G. Ya. Sharapova, A. A. Studnitsyn. Guide Book on Children Dermatology. Moscow, Medicina Publishing House, 1983, 476:64–66, 227, 314; in Russian). This effect may be enhanced by the addition of biologically active substances including vitamins, enzymes, amino acids, lecithin, tissues preparations, and other biologically active substances which stimulate skin metabolism and nutrition (N. B. Koroliova. In the: "Guide Book of Medicinal Cosmetology", ed. V. T. Glukbenki, Kyiv, Zdorovia Publishing House, 1989, 302: 86–97; in Russian). For patients with dry peeling skin with decreased turgor and elasticity, increased wrinkles and other indications of premature skin fading and aging, nutritional vitamin creams, such as vitamin A and E, are usually applied (T. V. Ptchiolkina, Ye. A. Sobolieva, I. G. Shishkina. In the: "Guide Book of Medicinal Cosmetology", Leningrad, Meditsina Publishing House, 1978, 176:15–16).

However, this well known vitamin-containing preparation does not assure a result because it does not have an adequate effect on tissues perfusion and nutritional homeostasis.

The preparation used in dermatology which is the most similar in its action to the preparation of the present invention contains the following: salicylic acid (2.4 mass %), lanolin (24.4 mass %), vaseline (24.4 mass %), vitamin A oil solution (24.4 mass %), and water (24.4 mass %) (Guide Book of Medicinal Cosmetology, ed. A. F. Abakhadze, Moscow, Medicina Publishing House, 1975, 253 p.p., p. 71). This preparation is aimed to abolish skin dryness, stiffness, and toughness caused by hyperkeratosis. Lanolin, vaseline and oil are used here as a fat ointment base, and vitamin A and salicylic acid, a oxybenzoic acid derivative, as skin ameliorating active substances.

The preparation has the defect of low effectiveness because:

- its action is only directed to the symptoms but not to the cause of the pathological condition;
- the substrate deficiency due to the changed skin trophic homeostasis is not taken into account;
- the role of some biologically active substances causing skin cell damage is also not taken into consideration; and
- the adequate skin trophic necessary for higher energy process levels to restore damaged tissue structures cannot be achieved using such an ointment.

DISCLOSURE OF THE INVENTION

The goal of this invention is to find an external skin preparation containing an adequate combination of components assuring a set of physiological events. The trophometabolic activity of the preparation increases, due to adequate ingredients ratio, causing a high trophoprotective effect followed by a stable restoration of skin physiological functions, thus suggesting that the preparation is effective.

Attaining such a goal is possible because the external skin preparation of the present invention contains a lipid ointment base, vitamin A and water, salicylic acid or its derivatives as an oxybenzoic acid derivative, D-camphor, biogenic GABAergic substances, biogenic dopaminergic substances, M-cholinolytics, pancreatin, ascorbic acid, pantothenic acid calcium salt, and vitamin D2. The mass % ratio of these compounds being the following:

| | |
|---|---|
| Lipid ointment base | 30.0–70.0 |
| Vitamin A (retinol acetate) | 0.1–0.3 |
| Salicylic acid or its derivatives | 0.5–1.6 |
| D-Camphor | 2.0–4.0 |
| Biogenic GABAergic substances | 0.8–1.5 |
| Biogenic dopaminergic substances | 0.8–1.5 |
| M-cholinolytics | 0.01–0.1 |
| Pancreatin | 1.0–2.0 |
| Ascorbic acid | 0.5–1.0 |
| Pantothenic acid calcium salt | 0.5–2.5 |
| Vitamin D2 (ergocalciferol) | 0.000625–0.00125 |
| Water | the remainder |

The proposed composition of dermotropic substances contains interacting components, such as salicylic acid or its derivatives, D-camphor, biogenic neuromediators, M-cholinolytics, pancreatin, and vitamins in adequate concentrations, results in increased trophic and biological activity of the proposed remedy composition to obtain the highest trophoprotective effect. The synergism of the components assures adequate vascular circulation, corrects both energy and plastic deficiencies, and restores trophic homeostasis, followed by the optimization of skin's metabolism and physiology. The complex of salicylic acid or its derivatives (mass % 0.5–1.6) in combination with D-camphor (mass % 2.0–4.0) are included into this skin cosmetic preparation to intensify microcirculation as well as for better blood circulation in skin tissue, better perfusion and quick transport of physiologically active substances contained in the preparation.

Salicylic acid, a high lipotropic compound, which readily loosens epidermic tissues, possesses an anti-inflammatory effect, optimizes vascular circulation, and promotes the penetration of the cosmetic biostimulators into different skin layers. The lipophilic and surface activity properties of D-camphor as well as its ability to penetrate into the skin and to normalize vascular tonicity interact with salicylic acid or its derivatives to assure not only better vascular circulation and perfusion but also increases the penetrating ability of other medical components contained in the preparation, thus accelerating the trophoprotective effect of the preparation. The clinical signs of the effect on the skin are: rosy, fresh and smooth look; the face looses its droopiness, the skin pigmentation becomes more regular, and some infiltrates disappear.

The use of lower per cent quantities or other ratios of salicylic acid or its derivatives and of D-camphor as compared to those indicated does not permit restoration of microcirculation so effectively and quickly. Further, the use of these substances in higher concentrations causes skin irritation due both to D-camphor's irritative effect and salicylic acid's keratolytic action.

The group of neurotropic substances including GABAergic substances, dopaminergic compounds and M-cholinolytics, (their mass % being 0.8–1.5, 0.8–1.5, and 0.01–0.1, respectively), is added to the dermatological cosmetic preparation in order to correct neuromediators imbalance as well as substrate deficiency, which are the basis for skin trophic damage as a result of its changing physiological patterns. The importance of the mentioned neuromediator correction results from the common brain and epidermis origin in the course of embryo development. Some structures similar in their function and morphology are present in human brain and epidermis; and there is histological data suggesting skin cells interaction with peripheral nerve fibers.

Some tissue metabolites, biogenic substances possessing neuromediatory GABAergic and dopaminergic effect, are neurotransmitters of basal brain ganglia, including those in the highest vegetative nerve centers (reticular formation and hypothalamus), which influence the catecholamines level. Dopamine which is derived from L-DOPA in the tissues, exerts trophic effects on GABAergic neurons, thus suggesting L-DOPA and GABA be used together. At the same time, the presence of L-DOPA and GABA in the preparation of this invention permits the partial correction of the substrate deficiency.

The simultaneous presence of M-cholinolytics (i.e. atropine sulfate, 0.01–0.1%), which blocks the cholinergic mediation of the vegetative nerve system permits the correction of the imbalance of the physiologically active substances appearing in damaged tissues.

All of these events favor skin trophic optimization and normalization of metabolic processes with the reactions of physiological and reparative regeneration becoming more marked. They are usually followed by epithelization and melanogenesis, edema is abolished, skin pigmentation becomes normal, the skin becomes rosy and flesh-colored, the tissue turgor increases, and the patients become cheerful and are in better spirits.

It is impossible to obtain such results without the use of some additional biologically active substances, such as GABAergic and dopaminergic compounds as well as M-cholinolytics in the concentrations mentioned above. Any decrease in the content of these substances as compared to those mentioned above, leads to lower trophic and restorative effects. At the same time, if concentrations of GABAergic compounds, dopaminergic ones, and M-cholinolytics exceed 1.5 mass %, 1.5 mass %, and 0.1 mass %, respectively, the restorative properties of the preparation are poor. Some patients even feel burning after the application of the preparation to the skin. The results of skin restoration due to the action of the compounds, GABAergic, dopaminergic substances and M-cholinolytics, become better after addition of biogenic stimulators as pancreatin and vitamins A, D2, ascorbic acid, and pantothenic acid calcium salt.

Pancreatin, a preparation containing enzymes, is included in the preparation at mass % 1.0–2.0. Pancreatin is a dried animal pancreas tissue. Its effect after application may be due not only to its enzymatic activity permitting, for instance, wound surface purification and scar resolution but also to its ability to control metabolic processes. So the introduction of pancreatin into the preparation of this invention combined with regulatory neurotropic GABAergic substances, dopaminergic ones and M-cholinolytics in the ratios indicated here results in the acceleration of its trophic and metabolic activity.

The decrease of pancreatin content below 1 mass % reduces the effect of the preparation of our invention and delays the beginning of the trophic and restorative effects. Increasing the pancreatin above 2 mass % does not accelerate the effectiveness of the preparation. Therefore, 1–2 mass % of this component is usually introduced into the preparation.

The mixture of water-soluble vitamins (ascorbic acid and pantothenic acid calcium salt, 0.5–1.0 and 0.5–2.5 mass %, respectively) and oil-solubles ones (A and D2, 0.1–0.3 and 0.000625–0.00125 mass %, respectively) added to the preparation accelerates its trophic effect.

It is also possible to add to the preparation of the invention an antihistaminic preparation, dimedrole (0.05–0.1 mass %), as a blocking agent inhibiting tissue damage mediators. In such a way, it is possible to increase the correction of the developed imbalance of physiologically active tissue substances.

The external trophoprotective preparation of our invention may also contain dimexide (1.0–3.0 mass %). This reagent, capable of penetrating biological membranes, is a good pilot of other compounds by helping other preparation components to penetrate skin without any difficulty and accelerating their activities and synergism. This is especially important for patients with dystrophic skin phenomena and tissue perfusial damages.

Any dermatological composition containing lipids, as well as natural and synthetic lipid-like substances (lanoline, spermaceti, cacao butter, bee wax, plant oils, vaseline etc.) may be suitable for the preparation of the invention. These substances are present in mass % of 30-7. Such an emulsified lipid system may be of "water-in-oil" or "oil-in-water" type.

In such a way, the marked trophoprotective properties of a given external skin preparation and its metabolic activities are due to synergism of the chosen drug combination of the present invention: neurotropic drugs (GABAergic and dopaminergic mediators, M-cholinergic neuroreceptor inhibitors), enzymes-containing preparation Pancreatin and vitamins supplemented with lipotropic substances and dimexide increasing medicative components penetrating ability after skin application of the drug composition of our invention.

The preparation of our invention may also contain any fragrant compound (0.5–1.5 mass %), such as rose oil, lavender oil etc., favoring this preparation for use as a dermatological cosmetic nutritional cream.

The external preparation of trophoprotective action is to be prepared as follows: D-Camphor is ground with fat to obtain a homogenous camphor-fat mass; the latter one is to be supplemented with vaseline (if it is added as an ingredient of the fat base) and salicylic acid or its derivatives. The ingredients are mixed with fats and are ground to obtain the camphor-salicylic-fat mixture until obtaining butter consistency (mixture 1).

All the components of the fat base—non-liquid fats and lipid-like substances (water-free lanoline, spermaceti, bee wax, emulsion waxes et al.) are to be completely dissolved in a water bath at a temperature of 70°–75° C. and then removed from the bath.

As the lipid preparation is ground continuously, the liquid solution of small amounts of GABAergic substances, pancreatin suspension in a water solution of pantothenic acid calcium salt, water solutions of M-cholinolytics, dopaminergic substances, ascorbic acid and also dimexide, if necessary, are added. In such a way it is possible to obtain an emulsified lipid complex containing active biological substances (mixture 2). Both mixtures 1 and 2 are mixed intensively followed by oil vitamin solution and flavor addition. To assure the higher stability of the emulsified system obtained, it is possible to use any adequate emulsifier. The dermatologic, cosmetic preparation with trophoprotective effect prepared in such a way is to be stored at +4°–8° C. in a glass container protecting it from light.

THE BEST WAY TO OBTAIN THIS INVENTION

While testing this external preparation with a trophoprotective effect, we prepared samples with varying component ratios, taking into consideration both physiochemical parameters as well as therapeutic and preventive properties of the preparation. Some examples of compositions prepared according to this invention are presented in the Table.

The components that are most well known and the most widely used in the field of cosmetic dermatology were used in preparing these samples. Thus, lanoline, vaseline, seed oil, spermaceti and bee wax were used as lipid ointment base; γ-aminobutyric acid was used as a GABAergic substance, L-DOPA as a dopaminergic substance; atropine sulfate was used as a M-cholinolytic and lavender oil as the fragrant agent.

All of the samples of the external dermatological cosmetic preparation are prepared according to prescriptions presented in the Table and are of good consistency and color. They possess high metabolic activity and trophoprotective effect, penetrate well into skin tissues, regulate the skin metabolism and restore skin physiological functions. If compositions 1, 4, 7, and 10 are used, the organoleptic effect is found to be retarded compared to other samples of this composition. At the same time, the use of samples 3, 6, 9, and 12 of the external dermatological cosmetic preparation caused in single cases a transient feeling of skin tingling. The optimal component ratios were shown to be contained in samples 2, 5, 8, and 11 causing the most favorable skin trophoprotective effect. However, taking into account some physiochemical parameters of the external dermatologic cosmetic preparation, its commodity properties and organoleptic effect, sample 11 is considered to be the optimum. It was found to be the best due to the quickest organoleptic results obtained, better cosmetic effects including better skin pigmentation, increased tissue turgor and skin elasticity as well as preparation stability.

Below we describe some examples of use of our external dermatological cosmetic preparation with trophoprotective effect.

EXAMPLE 1

The subject is a 45 year old woman. Her face was pale, puffy, with bags under her eyes, and her skin was of sallow complexion, with hyperpigmentation loci on cheek-bones and lateral neck surfaces. Soft tissues were of decreased elasticity. The skin was dry, exhausted and flabby, especially on the lower part of face and on the neck. Some deep and surface wrinkles were seen near eye angles, on the forehead and on the lower eyelids. Transversal neck wrinkles as well as fan-shaped upper lip wrinkles were also remarkable.

Cream face masks containing the preparation in composition #4 was used (see the Table).

The cream was applied on the clean face and neck skin for 30–40 min. The cream was then carefully removed from the skin using a soft paper napkin. This procedure was repeated daily for 30 days.

After 10–12 days of this treatment, a general improvement in the patient's appearance was detected, accompanied by tissue elasticity increasing and surface wrinkles smoothing, and the neck and face skin becoming brighter. By the end of the course of the cream masks treatment, the skin became more elastic, surface wrinkles were smoothed, forehead and nose-bridge wrinkles were already less deep, puffy face appearance disappeared, and bags under eyes were less. The face skin became rosy with regular color pigmentation, having lost its local hyperpigmentation.

No side effects, skin irritation, and allergic react ions were found during treatment.

Further observations showed that the effect of the skin physiological functions restoration was stable.

EXAMPLE 2

The subject was a 32 year old woman. The skin on her face, neck, and hands was dry and dehydrated and desquamation was seen on her forehead and chin. The patient experienced occasional itching. Tissue turgor was decreased and skin flaccidity was seen near the eyes, on the forehead and nose-bridge of the face. Some wrinkles are seen in the eye angles and lower eyelids. Face skin pigmentation was irregular because of local hypo- and depigmentation on the chin and temporal-orbital regions as well as hyperpigmentation around the mouth, on temporal region, on the right part of forehead near the hairline. Two years ago vitiligo was diagnosed. The patient was treated by a dermatologist, put on a diet, and had some inner trophotropic therapy courses.

Cream face masks containing the preparation in composition #9 was used (see the Table) and applied as described in Example 1, except that the duration of the course of treatment was 25 days.

In 5–7 days after beginning the treatment, improved tissue turgor was observed. The skin became "alive", elastic, less dry, of better appearance, and the contrast between hyper- and depigmented loci became less, with the hyperpigmentation zones becoming brighter. After the treatment course was finished, the skin was already elastic and smooth accompanied with the disappearance of the pruritus. The wrinkles near eye angles were smoothed, and those on the lower eyelids became less remarkable. A tendency was detected of skin pigmentation improvement. It became more regular as a result of hyperpigmented loci brightening and bright flesh-colored loci appearance in depigmentation regions.

During several first days of treatment using the composition 9 (see Table) the patient had the feeling of skin tingling.

EXAMPLE 3

The subject was a 52 year old woman. Her skin was dry, flaccid, and very thin. Tissue turgor was flabby and accompanied by upper and lower eyelid deformation (prolapsus and bags under eyes, respectively). Deep and surface wrinkles of forehead, eyes angles, and neck, hirsutism of the upper lip, and diffused face skin hyperpigmentation causing sallow skin complexion was also observed.

Cream face masks containing the preparation in composition #11 was used (see the Table), and applied as described in Example 1, except that the duration of the course of treatment was 28 days.

In 7–8 days after beginning the treatment, the organoleptic effect of the treatment, marked turgor improvement, smoothing of surface wrinkles, better skin integument pigmentation with gradually getting rosier, making the face more fresh looking. At the end of the treatment course, tissue turgor became satisfactory, skin was elastic, not dry, and the bags under eyes disappeared. Some deep wrinkles became less remarkable, the surface wrinkles around the eye angles were smoothed. The patient's face became fresh, with the skin more bright and rosy with decreased upper lip hirsutism.

No unpleasant feelings and side effects were recorded.

Further observations showed that the effect of skin restoration was stable.

TABLE

| Components | Samples of the external dermocosmetical remedy, mass % of components in them | | | | | |
|---|---|---|---|---|---|---|
| | 1 | 2 | 3 | 4 | 5 | 6 |
| Lanoline | 9.0 | 14.5 | 20.0 | 9.0 | 14.5 | 20.0 |
| Vaseline | 3.0 | 4.5 | 6.0 | 3.0 | 4.5 | 6.0 |
| Bee wax | 3.0 | 4.0 | 5.0 | 3.0 | 4.0 | 5.0 |
| Spermaceti | 5.0 | 7.5 | 10.0 | 5.0 | 7.5 | 10.0 |
| Stone oil | 10.0 | 19.5 | 29.0 | 10.0 | 19.5 | 29.0 |
| Vitamine A (retinol acetate) | 0.1 | 0.2 | 0.3 | 0.1 | 0.2 | 0.3 |
| Salicylic acid or its derivatives | 0.5 | 1.05 | 1.6 | 0.5 | 1.05 | 1.6 |
| d-Camphor | 2.0 | 3.0 | 4.0 | 2.0 | 3.0 | 4.0 |
| γ-aminobutyric acid | 0.8 | 1.15 | 1.5 | 0.8 | 1.15 | 1.5 |
| L-DOPA | 0.8 | 1.15 | 1.5 | 0.8 | 1.15 | 1.5 |
| Atropine sulfate | 0.01 | 0.055 | 0.1 | 0.01 | 0.055 | 0.1 |
| Pancreatin | 1.0 | 1.5 | 2.0 | 1.0 | 1.5 | 2.0 |
| Ascorbic acid | 0.5 | 0.75 | 1.0 | 0.5 | 0.75 | 1.0 |
| Calcium pantothenate | 0.5 | 1.5 | 2.5 | 0.5 | 1.5 | 2.5 |
| Vitamin D2 (ergocalciferol) | 0.000625 | 0.0009375 | 0.00125 | 0.000625 | 0.0009375 | 0.00125 |
| Dimedrole | — | — | — | 0.05 | 0.075 | 0.1 |
| Dimexide | — | — | — | — | — | — |
| Flavour substance | — | — | — | — | — | — |
| Water | all the rest | | | | | |

| Components | Samples of the external dermocosmetical remedy, mass % of components in them | | | | | |
|---|---|---|---|---|---|---|
| | 7 | 8 | 9 | 10 | 11 | 12 |
| Lanoline | 9.0 | 14.5 | 20.0 | 9.0 | 14.5 | 20.0 |
| Vaseline | 3.0 | 4.5 | 6.0 | 3.0 | 4.5 | 6.0 |
| Bee wax | 3.0 | 4.0 | 5.0 | 3.0 | 4.0 | 5.0 |
| Spermaceti | 5.0 | 7.5 | 10.0 | 5.0 | 7.5 | 10.0 |
| Stone oil | 10.0 | 19.5 | 29.0 | 10.0 | 19.5 | 29.0 |
| Vitamine A (retinol acetate) | 0.1 | 0.2 | 0.3 | 0.1 | 0.2 | 0.3 |
| Salicylic acid or its derivatives | 0.5 | 1.05 | 1.6 | 0.5 | 1.05 | 1.6 |
| d-Camphor | 2.0 | 3.0 | 4.0 | 2.0 | 3.0 | 4.0 |
| γ-aminobutyric acid | 0.8 | 1.15 | 1.5 | 0.8 | 1.15 | 1.5 |
| L-DOPA | 0.8 | 1.15 | 1.5 | 0.8 | 1.15 | 1.5 |
| Atropine sulfate | 0.01 | 0.055 | 0.1 | 0.01 | 0.055 | 0.1 |
| Pancreatin | 1.0 | 1.5 | 2.0 | 1.0 | 1.5 | 2.0 |
| Ascorbic acid | 0.5 | 0.75 | 1.0 | 0.5 | 0.75 | 1.0 |
| Calcium pantothenate | 0.5 | 1.5 | 2.5 | 0.5 | 1.5 | 2.5 |
| Vitamin D2 (ergocalciferol) | 0.000625 | 0.0009375 | 0.00125 | 0.000625 | 0.0009375 | 0.00125 |
| Dimedrole | 0.05 | 0.075 | 0.1 | 0.05 | 0.075 | 0.1 |
| Dimexide | 1.0 | 2.0 | 3.0 | 1.0 | 2.0 | 3.0 |
| Flavour substance | — | — | — | 0.5 | 1.0 | 1.5 |
| Water | all the rest | | | | | |

RESULTS OF CLINICAL AND EXPERIMENTAL INVESTIGATIONS

Clinical investigations of the preparation of the present invention was carried out with 120 patients (18–60 years old) having skin fading as well as very thin desquamated skin with spots, wrinkles, and damaged pigmentation. The results of the investigations show that the use of the nutritional preparation softened and maintained normal, dry and flaccid skin and inhibited its aging. After the treatment course using cream masks containing the preparation, the skin became less dry, the pruritus and any feeling of stiffness and edema disappeared, the skin became rosy, smooth, elastic, exhibited high turgor, smoothed small wrinkles and exhibited more regular pigmentation. The positive results of the dermatological cosmetic preparation for skin applications and its therapeutic and preventive properties were detectable in 5–7 days after the beginning of treatment with the favorable effects becoming more pronounced with a wider effect as treatment continued. A treatment course of 25–30 days with cream masks containing the preparation of the present invention assures the stable therapeutic effect.

The measurement of the skin temperature during cream-containing masks application shows that it was 2–3 degrees higher as compared to the temperature at the beginning of the mask treatment. The data concerning tissue electric resistance also prove that there is better circulation in the treated tissues.

The external preparation with trophoprotecting effect caused no unpleasant feelings as well as no skin irritation or allergic phenomena. No negative effect on skin morphological structures were found.

The electron microscopic investigations of volunteer skin biopsies suggest the presence of intracellular metabolism activation, such as increased quantity of active mitochondria and abundance of cytoskeleton elements. Some histochemical data concerning the increase of succinate dehydrogenase activity due to oxidation-reduction processes prove indirectly the intensification of energetic skin metabolism.

Detailed investigations concerning possible toxic properties of our dermatological cosmetic preparation preceded further clinical studies. These investigations were made both in chronic and acute experiments with rats and white mice. Our results prove the preparation investigated to be practically harmless, to possess no allergic properties and to demonstrate no negative effect on skin cells morphology and other organs of experimental animals.

And what is more—our data (of organoleptic, histochemical and histological studies) prove the pronounced ability of the preparation to optimize the cells' function and to restore normal skin physiology. So, we observed the increased growth of the animals' hair. In histological sections, the basal epidermal layer was seen containing epitheliocytes with round "fulfilled" nuclei rich in chromatin grains. In many hair follicles, in both the upper and lower parts of the external hair root sheath, epithelial cells were found containing basophilic cytoplasm and large "fulfilled" nuclei. This fact proves indirectly increased cell function. In the basal-cell layer of skin there was no coarsened interstitial tissue. Instead, tender collagen and reticular fibrils were seen with round cell elements among them represented by fibroblasts, macrophages and other mononuclears as well as many moderatly plethoric blood vessels. Our histochemical studies show increased succinate dehydrogenase activity in rat basal epidermis and skin adnexa suggesting indirectly the higher level of energy processes.

INDUSTRIAL USE

The preparation of trophoprotective effect possesses high activity and achieves good results in stable restoration of skin functions and physiology. The preparation may be successfully used as a dermatological cosmetic to abolish different skin deficiencies due to trophic and metabolism disorders, such as, skin aging and fading making it thin, dry, hard, rigid, desquamative, and decreased turgor and elasticity. The use of the preparation described here accompanied by internal trophotropic drugs brings also positive results in cases of pigmentation disorders due to vitiligo and melanoderma development.

We claim:

1. A dermatological composition for external use comprising the following components in the designated amounts (mass %):

| | |
|---|---|
| Lipid ointment base | 30.0–70.0 |
| Vitamin A (retinol acetate) | 0.1–0.3 |
| Salicylic acid or derivative thereof which enhances vascular circulation | 0.5–1.6 |
| D-camphor | 2.0–4.0 |
| GABAergic substance | 0.8–1.5 |
| Dopaminergic substance | 0.8–1.5 |
| M-cholinolytic | 0.01–0.1 |
| Pancreatin | 1.0–2.0 |
| Ascorbic acid | 0.5–1.0 |
| Pantothenic acid calcium salt | 0.5–2.5 |
| Vitamin D2 (ergocalciferol) | 0.000625–0.00125 |
| Water | remainder. |

2. The composition according to claim 1, wherein said biogenic GABAergic substance is aminobutyric acid, said dopaminergic substance is L-DOPA, and said M-cholinolytic is atropin sulfate.

3. The composition according to claim 1, further comprising an antihistaminic agent, as a tissue damage mediator blocker, in quantities of 0.05–0.1 mass %.

4. The composition according to claim 1, wherein said antihistaminic agent is dimedrole.

5. The composition according to claim 1, further comprising dimexide in quantities of 1.0–3.0 mass %.

6. The composition according to claim 1, further comprising a fragrant substance in quantities of 0.5–1.5 mass %.

* * * * *